(12) United States Patent
Goto et al.

(10) Patent No.: US 10,111,626 B2
(45) Date of Patent: Oct. 30, 2018

(54) X-RAY CT APPARATUS

(71) Applicant: Toshiba Medical Systems Corporation, Otawara-shi (JP)

(72) Inventors: Takahiro Goto, Utsunomiya (JP); Satoshi Saito, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 41 days.

(21) Appl. No.: 14/926,197

(22) Filed: Oct. 29, 2015

(65) Prior Publication Data
US 2016/0120486 A1 May 5, 2016

(30) Foreign Application Priority Data

Oct. 31, 2014 (JP) ................. 2014-223733

(51) Int. Cl.
*A61B 6/00* (2006.01)
*A61B 6/03* (2006.01)

(52) U.S. Cl.
CPC ............ *A61B 6/032* (2013.01); *A61B 6/5205* (2013.01); *A61B 6/5211* (2013.01); *A61B 6/542* (2013.01); *A61B 6/545* (2013.01)

(58) Field of Classification Search
CPC ..... A61B 6/032; A61B 6/5205; A61B 6/5211; A61B 6/542; A61B 6/545; A61B 6/4042; A61B 6/482; A61B 6/541; A61B 6/027; A61B 6/0457; A61B 6/06; A61B 6/4028; A61B 6/4035; A61B 6/405; A61B 6/4085; A61B 6/4241; A61B 6/4275; A61B 6/4441; A61B 6/4488; A61B 6/484; A61B 5/0402; A61B 5/0476; A61B 5/0488; A61B 5/055; A61B 5/7475; A61B 6/037; A61B 6/4417; A61B 6/5258; A61B 8/4416;

(Continued)

(56) References Cited

U.S. PATENT DOCUMENTS 6,185,271 B1 * 2/2001 Kinsinger ............... A61B 6/032
378/19
6,907,102 B1 * 6/2005 Sauer ..................... A61B 6/032
378/19

(Continued)

FOREIGN PATENT DOCUMENTS

JP 2009-118884 6/2009
WO WO 2010/087267 A1 8/2010

*Primary Examiner* — Irakli Kiknadze
(74) *Attorney, Agent, or Firm* — Oblon, McClelland, Maier & Neustadt, L.L.P.

(57) ABSTRACT

An X-ray computed tomography (CT) apparatus according to an embodiments includes collection circuitry, control circuitry and image generation circuitry. The collection circuitry collects a signal derived from X-rays emitted from an X-ray tube and transmitted through a subject. The control circuitry calculates a value of tube current to be supplied to the X-ray tube in a main scan, based on a first image acquired through a reconstruction process using the signal and a first filter, the signal being collected by the collection circuitry in a localizer scan. The image generation circuitry generates a second image as a localizer image through a reconstruction process using the signal and a second filter, the signal being collected by the collection circuitry in the localizer scan.

9 Claims, 9 Drawing Sheets

(58) Field of Classification Search
CPC ... A61B 5/0059; A61B 5/0536; A61B 6/4021; A61B 6/583; A61B 6/488; A61B 6/508
USPC ........ 378/4, 16, 19, 62, 98.8, 98.9; 382/131, 382/132
See application file for complete search history.

(56) References Cited

U.S. PATENT DOCUMENTS

| | | | | |
|---|---|---|---|---|
| 6,950,492 | B2* | 9/2005 | Besson | A61B 6/032 378/16 |
| 8,571,178 | B2* | 10/2013 | Sendai | A61B 6/4042 378/157 |
| 2006/0262896 | A1* | 11/2006 | Nishide | A61B 6/032 378/15 |
| 2008/0273778 | A1* | 11/2008 | Goto | G06T 11/006 382/131 |
| 2009/0147919 | A1* | 6/2009 | Goto | A61B 6/032 378/86 |
| 2011/0274240 | A1 | 11/2011 | Sugaya et al. | |

\* cited by examiner

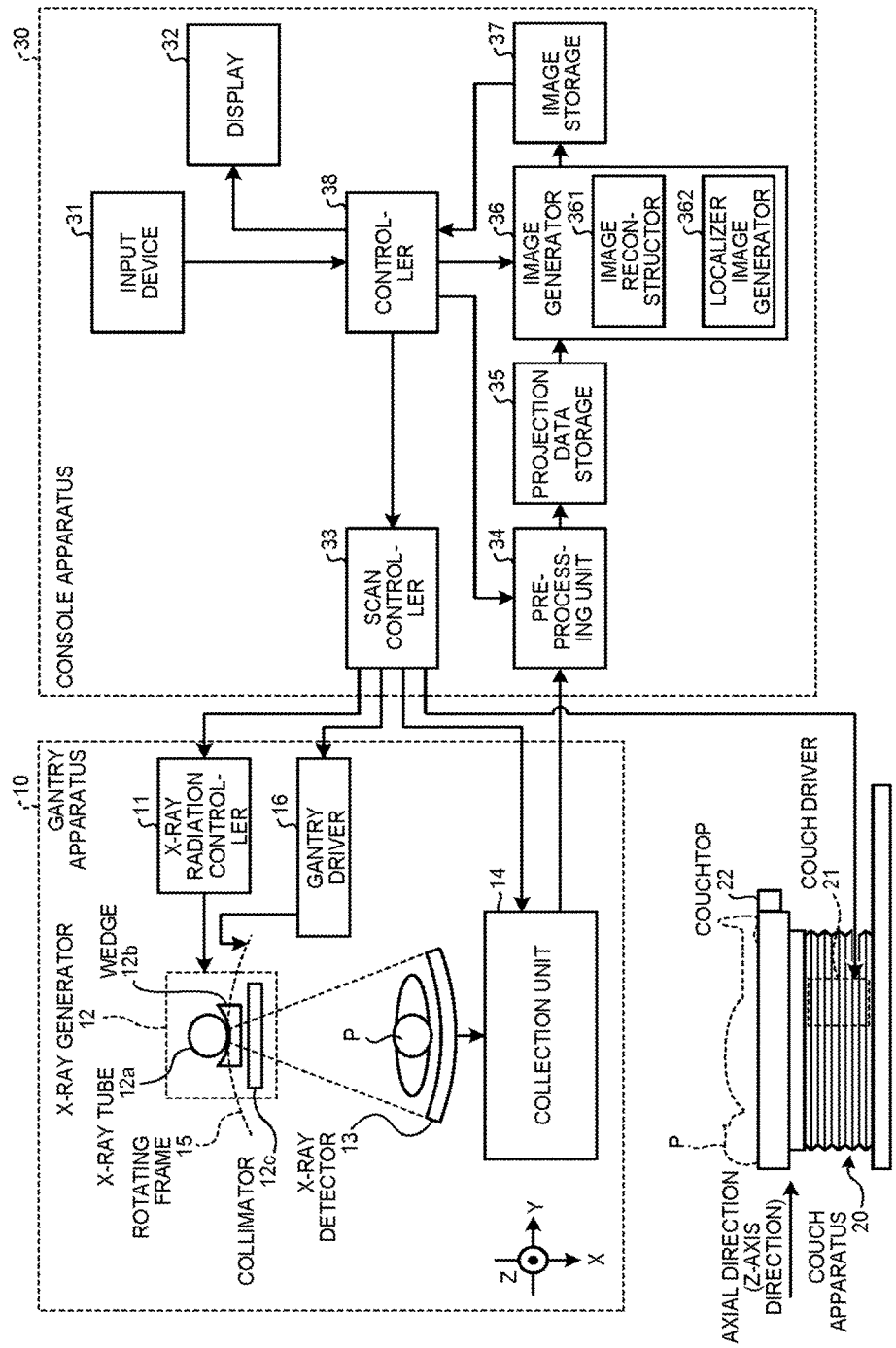

FIG.2A
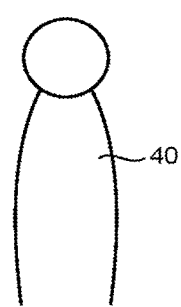 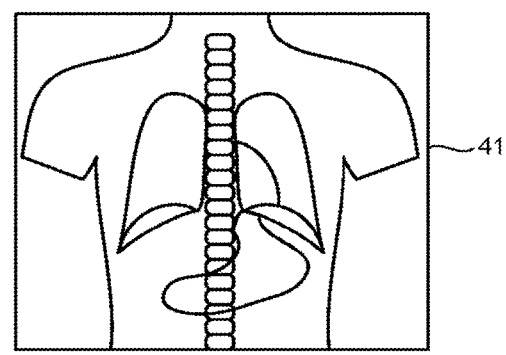
FIG.2B
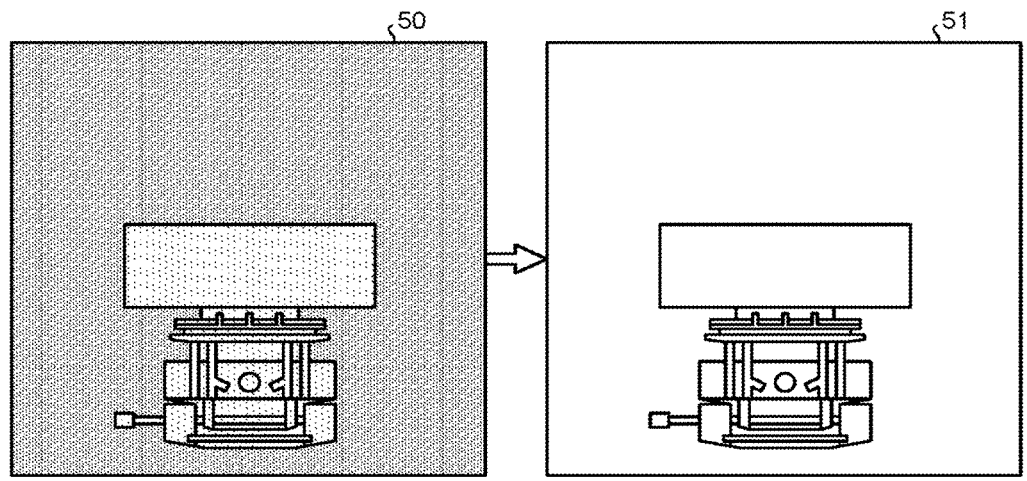

X-RAY CT APPARATUS

CROSS-REFERENCE TO RELATED APPLICATIONS

This application is based upon and claims the benefit of priority from Japanese Patent Application No. 2014-223733, filed on Oct. 31, 2014, the entire contents of which are incorporated herein by reference. The entire contents of the prior Japanese Patent Application No. 2015-211245, filed on Oct. 27, 2015, are also incorporated herein by reference.

FIELD

Embodiments described herein relate generally to an X-ray computed tomography (CT) apparatus.

BACKGROUND

In a scan by an X-ray CT apparatus, localizer scans for collecting localizer images (scano images) are conducted prior to the main scan. Further, these scans by the X-ray CT apparatus are subject to, for example, AEC (auto exposure control) for calculating the value of tube current to be supplied to an X-ray tube in the main scan, based on the collected localizer images.

A wide scanning range can be set to capture a localizer image because of recent increases in the number of arrayed detectors and the speed of couch movement. However, the pixel dimension of a localizer image varies according to the scanning range of the localizer image. This causes, for example, degradation of a localizer image scanned in a wide range, and may cause an error in the value of tube current calculated by AEC.

BRIEF DESCRIPTION OF THE DRAWINGS

FIG. 1 is a block diagram illustrating a configuration example of an X-ray CT apparatus according to an embodiment;

FIG. 2A, FIG. 2B, FIG. 3A, and FIG. 3B are diagrams illustrating localizer images generated by an X-ray CT apparatus according to the conventional art;

DETAILED DESCRIPTION

Figure 3A:
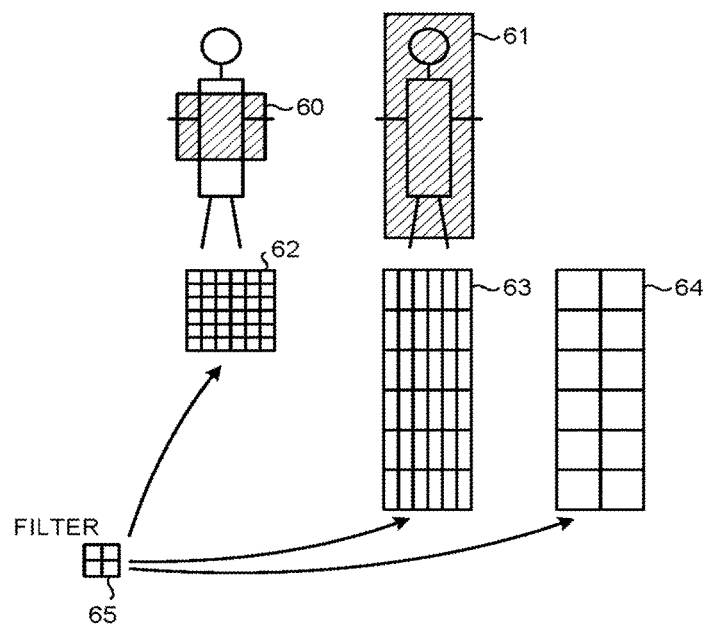

An X-ray computed tomography (CT) apparatus according to an embodiments includes collection circuitry, control circuitry and image generation circuitry. The collection circuitry collects a signal derived from X-rays emitted from an X-ray tube and transmitted through a subject. The control circuitry calculates a value of tube current to be supplied to the X-ray tube in a main scan, based on a first image acquired through a reconstruction process using the signal and a first filter, the signal being collected by the collection circuitry in a localizer scan. The image generation circuitry generates a second image as a localizer image through a reconstruction process using the signal and a second filter, the signal being collected by the collection circuitry in the localizer scan.

Embodiments of the X-ray CT apparatus will be described in details below with reference to the accompanying drawings. These embodiments are applicable to various types of X-ray CT apparatuses including a Rotate/Rotate-type apparatus having an X-ray tube and an X-ray detector integrally rotatable around a subject, and a Stationary/Rotate-type apparatus having a large number of fixed X-ray detecting elements arrayed in a ring form and an X-ray tube rotatable around a subject. In recent years, multi-tube X-ray CT apparatuses have been commercially available and its peripheral technology has been developed, in which a plurality of pairs of an X-ray tube and an X-ray detector are mounted on a rotatable frame. The present embodiment can be applied to either a conventional single-tube X-ray CT apparatus or a multi-tube X-ray CT apparatus. In the embodiments below, a Rotate/Rotate-type X-ray CT apparatus with a single tube will be described by way of example.

(Embodiment)

First of all, each unit of the X-ray CT apparatus according to an embodiment is schematically described. FIG. 1 is a block diagram illustrating a configuration example of the X-ray CT apparatus according to the embodiment. As illustrated in FIG. 1, the X-ray CT apparatus according to the embodiment has a gantry apparatus 10, a couch apparatus 20, and a console apparatus 30.

The gantry apparatus 10 is an apparatus that emits X-rays to a subject P and collects projection data from detection data of X-rays transmitted through the subject P. The gantry apparatus 10 includes an X-ray radiation controller 11, an X-ray generator 12, an X-ray detector 13, a collection unit 14, a rotatable frame 15, and a gantry driver 16.

The rotatable frame 15 supports the X-ray generator 12 including an X-ray tube 12a described later and the X-ray detector 13 rotatably around the subject P. The rotatable frame 15 is an annular frame that supports the X-ray generator 12 and the X-ray detector 13 opposed to each other with the subject P therebetween and is rotated fast on a circular orbit around the subject P by the gantry driver 16 described later.

The X-ray generator 12 is an apparatus that generates X-rays and emits the generated X-rays to the subject P. The X-ray generator 12 has an X-ray tube 12a, a wedge 12b, and collimator 12c.

The X-ray tube 12a emits X-rays. Specifically, the X-ray tube 12a is a vacuum tube that generates X-ray beams to the subject P with high voltage supplied by the X-ray radiation controller 11 described later. The X-ray tube 12a emits the X-ray beams to the subject P while the rotatable frame 15 is rotating. The X-ray tube 12a generates the X-ray beams expanding at a fan angle and a cone angle.

The wedge 12b is an X-ray filter for adjusting an X-ray dose of X-rays emitted from the X-ray tube 12a. The collimator 12c is a slit for narrowing the radiation range of X rays with the X-ray dose adjusted by the wedge 12b under control of the X-ray radiation controller 11 described later.

The X-ray radiation controller 11 is an apparatus serving as a high voltage generator that supplies high voltage to the X-ray tube 12a. The X-ray tube 12a generates X-rays using the high voltage supplied from the X-ray radiation controller 11. The X-ray radiation controller 11 adjusts the X-ray dose applied the subject P by adjusting tube voltage and tube current supplied to the X-ray tube 12a. The X-ray radiation controller 11 also adjusts the radiation range of X-rays (the fan angle and the cone angle) by adjusting the aperture of the collimator 12c.

Under control of the X-ray radiation controller 11, the X-ray tube 12a can continuously emit X-rays around the entire periphery of the subject P for full reconstruction or can continuously emit X-rays for half reconstruction in a radiation range that enables the half reconstruction (180 degrees+ fan angle). Under control of the X-ray radiation controller 11, the X-ray tube 12a can intermittently emit X-rays (pulse X-rays) at a preset position (tube position). The X-ray radiation controller 11 also can modulate the intensity of X-rays emitted from the X-ray tube 12a. For example, the X-ray radiation controller 11 increases the intensity of X-rays emitted from the X-ray tube 12a at a particular tube position and reduces the intensity of X-rays emitted from the X-ray tube 12a in a range excluding the particular tube position. The tube position refers to the position of the X-ray tube 12a on the circular orbit around the subject P. The position (tube position, tube angle) of the X-ray tube 12a illustrated in FIG. 1 is hereinafter defined as "0 degree (360 degrees)". The tube positions (tube angles) are hereinafter defined as "0 degree, . . . , 90 degrees, . . . , 180 degrees, . . . , 270 degrees, . . . , 360 degrees" clockwise in the circumferential direction of the rotatable frame 15 illustrated in FIG. 1.

The gantry driver 16 allows the X-ray generator 12 and the X-ray detector 13 to turn on the circular orbit around the subject P by rotatably driving the rotatable frame 15.

The X-ray detector 13 detects X-rays emitted from the X-ray tube 12a and transmitted through the subject P. Specifically, the X-ray detector 13 detects the X-rays emitted from the X-ray tube 12a and transmitted through the subject P with X-ray detecting elements arranged in two dimensions. The X-ray detector 13 illustrated in FIG. 1 is a two-dimensional array detector (planar detector) that outputs X-ray intensity distribution data representing the intensity distribution of X-rays transmitted through the subject P. In the X-ray detector 13, a plurality of rows of X-ray detecting element (detecting element rows) arranged in a channel direction (the Y-axis direction illustrated in FIG. 1) are arranged in the axial direction of the subject P (the axis direction illustrated in FIG. 1). For example, the X-ray detector 13 has 320 rows of detecting elements arranged in the axial direction of the subject P for detecting intensity distribution data of X-rays transmitted through the subject P in a wide range. The axial direction may be called a slice direction.

The collection unit 14 is a DAS (data acquisition system) that collects projection data from detection data of X-rays detected by the X-ray detector 13. For example, the collection unit 14 performs amplification processing, A/D conversion processing, inter-channel sensitivity correction processing, and other processing on the X-ray intensity distribution data detected by the X-ray detector 13 to generate projection data and transmits the generated projection data to the console apparatus 30 described later. For example, when X-rays are continuously emitted from the X-ray tube 12a during rotation of the rotatable frame 15, the collection unit 14 collects a projection data group corresponding to the entire periphery (corresponding to 360 degrees). The collection unit 14 associates each of the collected projection data with a tube position and transmits the associated data to the console apparatus 30 described later. The tube position serves as information indicating the projection direction of the projection data. The inter-channel sensitivity correction processing may be performed by a pre-processing unit 34 described later.

The couch apparatus 20 is an apparatus on which a subject P lies and includes a couchtop 22 and a couch driver 21. The couchtop 22 is a plate on which the subject P lies. The couch driver 21 moves the subject P into the rotatable frame 15 (within an imaging space) by moving the couchtop 22 in the Z-axis direction under control of a scan controller 33 described later.

The gantry apparatus 10 executes a helical scan, for example, in which the subject P is helically scanned by rotating the rotatable frame 15 while moving the couchtop 22 during the main scan. Alternatively, the gantry apparatus 10 executes a conventional scan in which the subject P is scanned on the circular orbit by rotating the rotatable frame 15 with the position of the subject P kept fixed after moving the couchtop 22 during the main scan. Alternatively, the gantry apparatus 10 executes a step-and-shoot method in which a conventional scan is performed in a plurality of scan areas by moving the position of the couchtop 22 at regular intervals during the main scan.

In a test with the X-ray CT apparatus, localizer scan (scanogram collection) is performed before the main scar. A localizer scan is a scan performed prior to the main scan in order to appropriately capture an image in the range of an organ of interest. A user makes a scan plan by referring to the localizer image (scanogram) obtained through a localizer scan. The user then allows the X-ray CT apparatus to execute the main scan in accordance with the scan plan and capture an image in the range of the organ of interest.

In a localizer scan, a scanogram is captured by scanning the whole body of the subject P along the axial direction, for example, by moving the couchtop 22 with the rotatable frame 15 being rotated while X-rays are emitted from the X-ray tube 12a. A scan plan may be made using a single localizer image obtained by performing a localizer scan in one direction. Alternatively, a scan plan may be made using a plurality of localizer images obtained, for example, by performing localizer scans in a plurality of directions.

In the case where a localizer scan is performed in one direction, for example, imaging is performed in the direction of "90 degrees" of the tube position depending on the size of the imaging target. In the case where a localizer scan is performed in a plurality of directions, for example, a localizer scan is performed in the orthogonal two directions, namely, the direction of "0 degree" of the tube position and the direction of "90 degrees" of the tube position.

In a localizer scan, for example, a scanogram may be captured by helically scanning the whole body of the subject P along the axial direction by moving the couchtop 22 with the rotatable frame 15 being fixed while emitting X-rays from the X-ray tube 12a. In this case, for example, the collection unit 14 collects a projection data group for a localizer image in association with tube positions when the tube position of the X-ray tube 12a on the rotatable frame 15 being rotated reaches a particular position, for example, the direction of "0 degree" and when the tube position reaches the direction of "90 degrees".

The collection unit 14 collects a projection data group for a localizer image in association with tube positions and transmits the projection data group to the console apparatus 30 described later during a localizer scan. Embodiments are not limited to the foregoing example. For example, the gantry apparatus 10 may be moved, rather than moving the couchtop 22, or both of the couchtop and the gantry apparatus 10 may be moved.

The console apparatus 30 is an apparatus that receives an operation on the X-ray CT apparatus by an operator and reconstructs X-ray CT image data from X-ray detection data collected by the gantry apparatus 10. The console apparatus 30 includes an input device 31, a display 32, the scan controller 33, the pre-processing unit 34, a projection data storage 35, an image generator 36, an image storage 37, and a controller 38.

The input device 31 includes a mouse, a keyboard, a button, and a pedal (foot switch) used by the operator of the X-ray CT apparatus for inputting various instructions and settings, and transfers information of the received instructions or settings from the operator to the controller 38.

The display 32 is a monitor referred to by the operator, plays X-ray CT image data or a localizer image (scanogram) to the operator under control of the controller 38, and displays a GUI (graphical user interface) for receiving variety of instructions, settings and others from the operator through the input device 31. For example, the operator inputs test information such as a posture during imaging of the subject P lying on the couchtop 22 to the GUI for test information registration, using the input device 1.

The scan controller 33 controls the process of collecting projection data in the gantry apparatus 10 by controlling the operation of the X-ray radiation controller 11, the gantry driver 16, the collection unit 14, and the couch driver 21 under control of the controller 38 described later. In a localizer scan, when the controller 38 described later calculates the value of tube current to be supplied to the X-ray tube 12a in the main scan using the localizer image, the scan controller 33 receives the calculated value from the controller 38 and controls the operation of the X-ray radiation controller 11. When the controller 38 described later calculates a couch movement distance using the localizer image, the scan controller 33 receives the calculated couch movement distance from the controller 38 and controls the operation of the couch driver 21.

The pre-processing unit 34 performs logarithmic transformation processing and correction processing such as offset correction, sensitivity correction, and beam hardening correction on the projection data generated by the collection unit 14 during the main scan to generate the corrected projection data (also called raw data). The corrected projection data on the main scan generated by the pre-processing unit 34 is hereinafter referred to as projection data for reconstruction. The pre-processing unit 34 also performs similar processing on the projection data generated by the collection unit 14 during a localizer scan to generate the corrected projection data (raw data). The corrected projection data on a localizer image generated by the pre-processing unit 34 is hereinafter referred to as projection data for a localizer image.

The projection data storage 35 stores the projection data for reconstruction and the projection data for a localizer image generated by the pre-processing unit 34. The projection data storage 35 also stores the projection data collected by the collection unit 14 per se. The projection data storage 35 stores the tube positions associated with the projection data generated by the pre-processing unit 34 and the projection data generated by the collection unit 14.

The image generator 36 is a processing unit that generates a variety of image data using projection data stored in the projection data storage 35 and includes an image reconstructor 361 and a localizer image generator 362 as illustrated in FIG. 1.

The image reconstructor 361 reconstructs X-ray CT image data using the projection data for reconstruction stored in the projection data storage 35. There are a variety of reconstruction methods, for example, including back projection processing. Examples of the back projection processing include back projection processing by FBP (filtered back projection). Alternatively, the image reconstructor 361 may reconstruct X-ray CT image data using iterative approximations.

The image reconstructor 361 can reconstruct three-dimensional X-ray CT image data using projection data collected by helical scanning, conventional scanning using the X-ray detector 13 that is a planar detector, or conventional scanning by the step-and-shoot method. For example, the image reconstructor 361 reconstructs three-dimensional X-ray CT image data as a plurality of axial cross-sectional image data. The cross-sectional image data can be used as two-dimensional X-ray CT image data for display. The image reconstructor 361 performs a variety of rendering processing on three-dimensional X-ray CT image data to generate two-dimensional image data for display. An example of the rendering processing is a process of reconstructing MPR (multi planar reconstruction) image data of any given cross section from three-dimensional X-ray CT image data by MPR. Another example of the rendering processing is a process of generating VR image data or MIP image data that reflects three-dimensional information, from three-dimensional X-ray CT image data by volume rendering or MIP (maximum intensity projection).

The localizer image generator 36 generates a localizer image using the projection data for a localizer image stored in the projection data storage 35 or the projection data (projection data before processing by the pre-processing unit 34) generated by the collection unit 14 during a localizer scan and stored in the projection data storage 35. In the present embodiment, the localizer image generator 362 performs first image processing described later on the signal collected by the collection unit 14 in a localizer scan to generate a first localizer image that is an image for calculation for the controller 38 to calculate the value of tube current to be supplied to the X-ray tube 12a in the main scan. The localizer image generator 362 also performs second image processing described later on the signal collected by the collection unit 14 in localizer imaging to generate a second localizer image that is a display image. The first localizer image that is an image for calculation and the second localizer image that is a display image have a constant pixel dimension irrespective of the scanning range in a localizer scan. The details of processing performed by the localizer image generator 362 will be described later.

The controller 38 performs overall control of the X-ray CT apparatus by controlling the operations of the gantry apparatus 10, the couch apparatus 20, and the console apparatus 30. Specifically, the controller 38 control a scan performed in the gantry apparatus 10 by controlling the scan controller 33. The controller 38 also controls an image reconstruction process and an image generation process in the console apparatus 30 by controlling the pre-processing unit 34 and the image generator 36. The controller 38 also controls the display 32 to display a variety of image data stored in the image storage 37 on the display 32. The controller 38 performs AEC (auto exposure control). In the present embodiment, the controller 38 calculates the value of tube current to be supplied to the X-ray tube 12a in the main scan, using the first localizer image that is an image for calculation generated by the localizer image generator 362 in a localizer scan. The controller 38 also calculates the value of the couch movement distance, using the first localizer image or the second localizer image generated by the localizer image generator 362 in a localizer scan. The controller 38 transmits the calculated value of tube current to the scan controller 33. The controller 38 transmits the calculated value of the couch movement distance to the scan controller 33. The details of the processing performed by the controller 38 will be described later.

The localizer images generated by an X-ray CT apparatus according to the conventional art will now be described with reference to FIG. 2A to FIG. 3B.

FIG. 2A to FIG. 3B are diagram illustrating localizer images generated by the X-ray CT apparatus according to the conventional art. An imaging target 40 in the left diagram in FIG. 2A represents the subject P. The right diagram in FIG. 2A represents a localizer image 41 captured using the X-ray CT apparatus according to the conventional art. For example, the bones, blood vessels, and organs of the subject P are visualized in the localizer image 41. Their outlines are visualized in an enhanced manner in the localizer image 41.

The outlines are visualized in an enhanced manner for the following reasons. First, the signal includes some noise. In order to accurately visualize the outline of, for example, an organ in the presence of noise, an image processing filter such as an edge detection filter is used to visualize the outline of the organ in the conventional localizer image generation process. For example, a difference filter that simply obtains the difference between adjacent pixels or a variety of primary differential filters may be used as the image processing filter to perform edge detection, or a secondary differential filter such as a Laplacian filter may be used to perform edge detection. By using such an image processing filter, the structural features such as bones, blood vessels, and organs of the subject P are efficiently extracted, so that the user can understand their outlines with high visibility.

In AEC, for example, the amount of current to be supplied to the X-ray tube 12*a* in the main scan is determined based on a localizer image. In the conventional art, however, an error occurs in calculating the amount of current to be supplied to the X-ray tube 12*a* in the main scan, because the signal values of the outlines of the organ and others are overestimated (enhanced) in generating a localizer image due to the use of an image processing filter such as an edge detection filter. For example, if tube current calculation is carried out with a localizer image for display generated according to the conventional art, the calculated tube current may be high for a position with a steep change in pixel value due to the effect of an image filter.

FIG. 2B is a diagram illustrating the feature of a localizer image generated by the X-ray CT apparatus according to conventional art, in an example in which an X-ray phantom is imaged. An image 50 illustrated in the left diagram in FIG. 2B is a typical example of the localizer image generated for the X-ray phantom as an imaging target. An image 51 illustrated in the right diagram in FIG. 2B derives from the image 50 in FIG. 2B with the image contrast adjusted. As can be understood from FIG. 2A and FIG. 2B, in the conventional art, the pixel value of an outline portion in the localizer image is enhanced and overestimated due to the effect of an image processing filter.

FIG. 3A is a diagram illustrating the feature of a localizer image generated by the X-ray CT apparatus according to the conventional art, in a point of view different from FIG. 2A and FIG. 2B. The upper two diagrams in FIG. 3A illustrate an example in which a localizes scan is performed for the same subject P. The scanning ranges of the localizes imaging are different between the left and right diagrams. The left diagram illustrates a case where the scanning range is "small" as in a scanning range 60. The right diagram illustrates a case where the scanning range is "large" as in a scanning range 61.

For the sake of explanation, in the case of the scanning range "small", the scanning range in the channel direction (horizontal direction) is 512 mm, and the scanning range in the axial direction (vertical direction) is 512 mm, by way of example. In the case of the scanning range "large", the scanning range in the channel direction is 512 mm, and the scanning range in the axial direction is 1536 mm, by way of example.

In the conventional art, a localizer image is generated using a prefixed "matrix size", irrespective of the scanning range of the localizer image. The matrix size is, for example, 128, 256, 512, and 1024 or 10, 100, and 1000. For example, "the matrix size in the channel direction is 512" means that there are 512 pixels in the channel direction.

For example, "the matrix size in the axial direction is 512" means that there are 512 pixels in the axial direction. For example, if the matrix size in the channel direction is 512 and the matrix size in the axial direction is 512, a localizes image is generated using 512×512=262144 pixels. In the following, in the example in FIG. 3A, the matrix size in the channel direction is 512, and the matrix size in the axial direction is 512.

The following relational expressions hold between the "pixel dimension", which is the dimension of a region corresponding to each pixel, the "matrix size", and the "scanning range". The relational expression (1) is "the scanning range in the channel direction=the pixel dimension in the channel direction×the matrix size in the channel direction". The relational expression (2) is "the scanning range in the axial direction=the pixel dimension in the axial direction×the matrix size in the axial direction".

For example, in the case of the scanning range "small" as in the scanning range 60 in FIG. 3A, if the scanning range in the channel direction is 512 mm, the scanning range in the axial direction is 512 mm, and the matrix size in the channel direction and the matrix size in the axial direction are both 512, the pixel dimension is 512 mm/512=1 mm both in the channel direction and in the axial direction. A matrix 62 in FIG. 3A illustrates such a situation, that is, a case where the pixel dimension is small both in the channel direction and in the axial direction.

The case of the scanning range "large" as in the scanning range 61 in FIG. 3A will now be discussed. In this case, the scanning range in the channel direction is 512 mm, the scanning range in the axial direction is 1536 mm, and the matrix size in the channel direction and the matrix size in the axial direction are both 512. Based on these, the pixel dimension is 512 mm/512=1 mm in the channel direction and 1536 mm/512=3 mm in the axial direction.

In other words, the pixel dimension in the axial direction becomes large in the conventional art. A matrix 63 in FIG. 3A illustrates a situation, that is, an example in which the pixel dimension is small in the channel direction whereas it is large in the axial direction. Since the scanning range is large in the axial direction, when localizer image is generated with the same matrix size as in the case of the scanning range "small", the pixel dimension in the axial direction is inevitably increased. As a result, the image resolution in the axial direction is degraded.

In the conventional art, in the case of the scanning range "large", for example, when the pixel dimension is 1 mm in the channel direction and 3 mm in the axial direction as described above, for example, the pixel dimension in the channel direction is set to 3 mm and the pixel dimension in the axial direction is set to 3 mm in order to keep the aspect ratio of each pixel.

A matrix 64 in FIG. 3A illustrates such a situation, that is, an example in which the pixel dimension is increased both in the channel direction and in the axial direction. In the case where the scanning range is large in the axial direction, when a localizer image is generated with the same matrix size as in the case of the scanning range "small" and the aspect ratio of each pixel is fixed irrespective of the scanning range, the pixel dimensions in the channel direction and the axial direction are inevitably increased. As a result, the image resolution in the channel direction and the axial direction is degraded.

More specifically, in the conventional art, a localizer image is generated using a prefixed matrix size, irrespective of the dimension of the scanning range. A wide scanning range can be set to capture a localizer image because of recent increases in the number of arrayed detectors and the speed of couch movement. In the conventional art, however, an increased scanning range increases the pixel dimension and degrades an image because the matrix size used is prefixed irrespective of the dimension of the scanning range.

In addition, when the pixel dimension changes according to a change in the scanning range, an error (artifact) occurs in calculation of tube current to be supplied to the X-ray tube 12a in the main scan. This will be described in more details.

An image processing filter 65 in FIG. 3A schematically represents a filter used in the process of calculating the tube current to be supplied to the X-ray tube 12a in the main scan. An original signal for localizer imaging includes some noise. For example, a smoothing filter is used in order to remove the effects of the noise and correctly calculate the value of tube current to be supplied to the X-ray tube 12a in the main scan. The signal intensity free from the effects of noise can be obtained by spatially averaging the signal intensity using the smoothing filter. Examples of the smoothing filter include a moving average filter that adds signals from a predetermine number of neighboring pixels together to obtain an average, a Gaussian filter, a low-pass filter, and a nonlinear filter. With the moving average filter, for example, a filtered signal value is the value of moving average of three points in each of the channel direction and the axial direction. In this case, in total, values at 3×3=9 points are added together and averaged. Alternatively, the filtered signal values may be the value of moving average of 10 points in each of the channel direction and the axial direction. In this case, in total, values at 10×10=100 points are added together and averaged. The image processing filter 65 schematically represents such a situation. The image processing filter 65 is a filter suitable for the pixel dimension for the matrix 62.

In the conventional art, an error occurs in calculating value of tube current to be supplied to the X-ray tube in the main an, because the same filter is used irrespective of the scanning range in a filter process even after the scanning range is changed and the pixel dimension is changed. For example, the image processing filter 65 is a filter suitable, for the pixel dimension for the matrix 62 but not suitable for the pixel dimension for the matrix 63 or the matrix 64. Accordingly, if a smoothing process is performed using the image processing filter 65 in a situation in which the pixel dimension is as in the matrix 63 or the matrix 64, an error occurs in calculating the tube current.

In order to solve this problem, for example, the image processing filter 65 may be changed according to the changing scanning range. It is, however, difficult to appropriately change the image processing filter 65 according to the changing scanning range for each localizer scan. This will be described specifically. For example, it is assumed that a filter is used which calculates the moving average of three points in each of the channel direction and the axial direction in the first scanning range. It is assumed that the pixel dimension increases by a factor of 1.1 as a result of imaging in the second scanning range. Since the number of points from which a moving average is calculated has to be an integer, a filter that calculates a moving average of 3×1.1=3.3 points cannot be used but a filter that calculates a moving average of three points or a filter that calculates a moving average of four points must be used. It is therefore difficult to appropriately change the image processing filter 65 according to the changing scanning range.

Figure 3B:
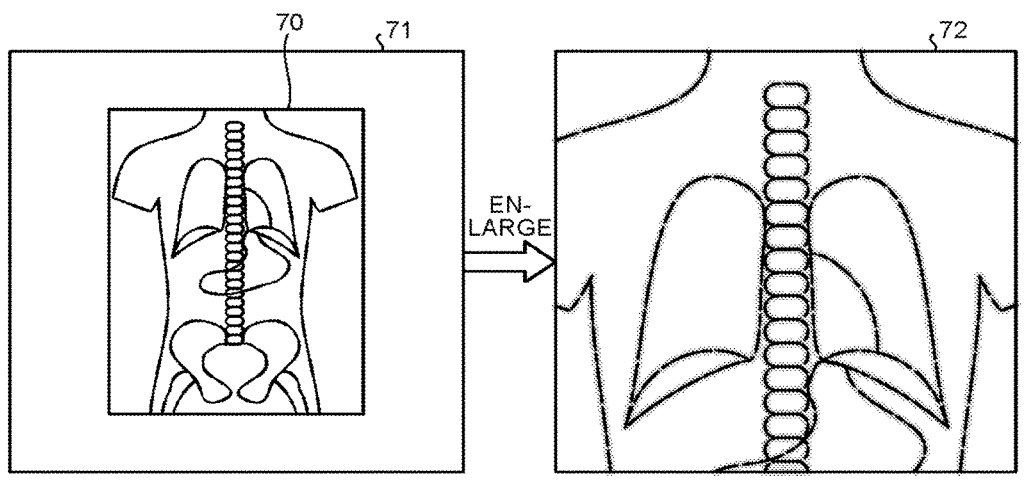

FIG. 3B is a diagram illustrating the feature of a localizer image generated by the X-ray CT apparatus according to the conventional art, in an example in which the subject P is an imaging target. The left diagram in FIG. 3B illustrates a localizer image 70 generated at a matrix size in which the entire scanning range fits, for example, on a display screen 71 corresponding to a 512×512 matrix. In the left diagram in FIG. 3B, since the matrix size in which the entire scanning range fits is used, the localizer image 70 appears in a reduced size and a region without image data additionally appears on the display screen 71. An image 72 on the right in FIG. 3B is a partial region of the localizer image 70 in an enlarged size. As can be understood by comparison with FIG. 5B described later, in the conventional art, the increased dimension of the scanning range causes an increase in the pixel dimension and degrades the image quality of the localizer image. As a result, an error occurs in calculating the value of tube current. In the conventional art, the increase in pixel dimension degrades the localizer image for display as well.

In the present embodiment, therefore, the localizer image generator 362 generates a localizer image having a constant pixel dimension irrespective of the scanning range in a localizer scan, using a signal collected by the collection unit 14 in a localizer scan. The controller 38 then calculates the value of tube current to be supplied to the X-ray tube 12a in the main scan, using the localizer image described above. Specifically, the localizer image generator 362 generates the first localizer image for the controller 38 to calculate the value of tube current and the second localizer image to be displayed to the user, using the signal collected by the collection unit 14 in a localizer scan. The controller 38 calculates the value of tube current using the first localizer image.

For example, the localizer image generator 362 generates the first localizer image by performing the first image processing that does not enhance the outline of the imaging target and generates the second localizer image by performing the second image processing that enhances the outline of the imaging target. As an example, the localizer image generator 362 performs the first image processing using a smoothing process and performs the second image processing using a process including an edge detection process. The localizer image generator 362 may concurrently generate the first localizer image and the second localizer image or may sequentially generate them in any given order.

The controller 38 calculates the thickness of the subject P and the distance over which the subject P is moved from a position in a localizer scan to the center of the effective field of view in the main scan, using theses localizer images, and calculates the value of tube current based on the calculated thickness and distance. The controller 38 performs localizer scans in a plurality of directions and calculates the value of tube current using the respective localizer images in those directions generated by the localizer image generator 362.

The localizer images generated by the X-ray CT apparatus according to the embodiment will now be described below with reference to FIG. 4A to FIG. 5C. FIG. 4A to FIG. 5C are diagrams illustrating the localizer images generated by the X-ray CT apparatus according to the embodiment.

Figure 4A:
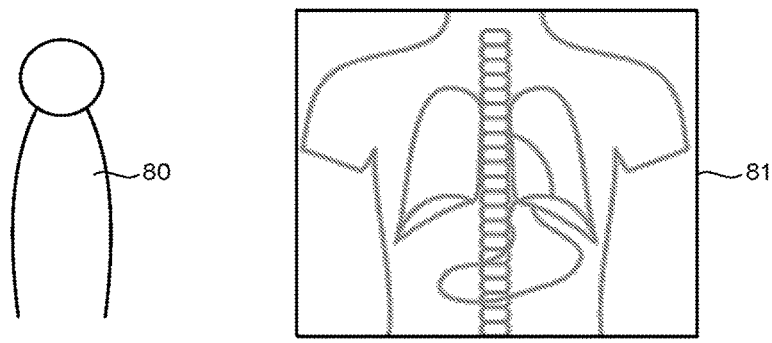
FIG. 4A, FIG. 4B, FIG. 5A, FIG. 5B, and FIG. 5C are diagrams illustrating localizer images generated by the X-ray CT apparatus according to the embodiment.

An imaging target 80 in the left diagram in FIG. 4A represents the subject P. The right diagram in FIG. 4A represents a first localizer image 81 according to the embodiment. For example, the bones, blood vessels, and organs of the subject P are visualized as a localizer image in the first localizer image 81.

In this embodiment, the localizer image generator 362 generates the first localizer image by performing image processing that does not enhance the outline of the imaging target, using the signal collected by the collection unit 14. That is, the first localizer image 81 generated in the embodiment is a localizer image in which no enhancement occurs internally. The right diagram in FIG. 4A illustrates a localizer image in which, unlike the localizer image 41 in the right diagram in FIG. 2A, the outline of the imaging target is not enhanced in the first localizer image 81.

An example of the image processing that does not enhance the outline of the imaging target is a smoothing filter process performed on the signal collected by the collection unit 14. Examples of the smoothing filter process include the processing using a moving average filter, a Gaussian filter, a low-pass filter, a nonlinear filter, and other filters.

Another example of the image processing that does not enhance the outline of the imaging target is a process of performing identity transformation on the signal collected by the collection unit 14. In such a case, the localizer image generator 362 does not perform any filter process on the signal collected by the collection unit 14.

Another example of the image processing that does not enhance the outline of the imaging target is a combination of an edge detection process of applying a filter for detecting the outline to the signal collected by the collection unit 14 using a variety of edge detection filters such as a difference filter, a differential filter, and a Laplacian filter, and an anti-aliasing process subsequently performed on the detected edge to blur the outline.

The localizer image generator 362 performs such image processing to generate the first localizer image in which the outline of the imaging target is not enhanced. This configuration yields a reduced error in calculation of the value of the current to be supplied to the X-ray tube 12a in the main scan.

Figure 4B:
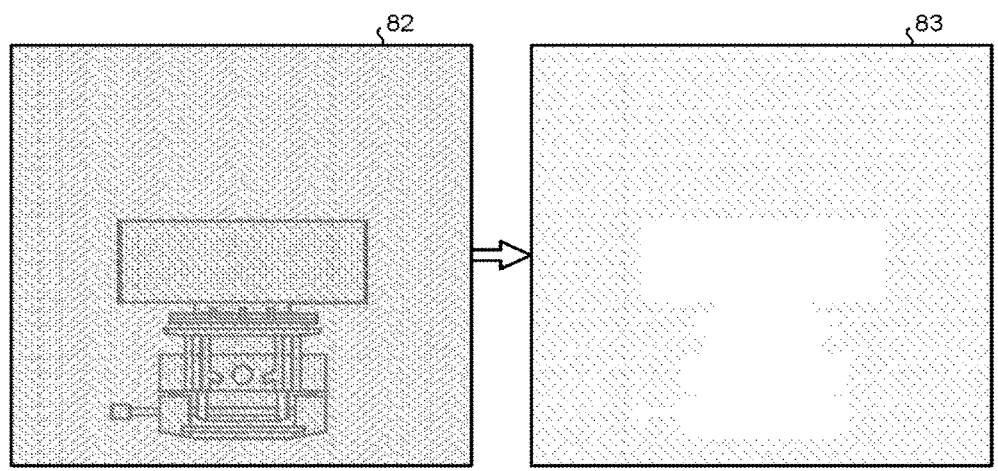

FIG. 4B is a diagram illustrating the feature of a localizer image generated by the X-ray CT apparatus according to the embodiment, in an example in which an X-ray phantom is an imaging target. An image 62 illustrated in the left diagram in FIG. 4B is an example of the first localizer image generated for an X-ray phantom as the imaging target. An image 83 illustrated in the right diagram in FIG. 4B derives from the image 82 with the image contrast adjusted. As can be understood from FIG. 4A and FIG. 4B, in the embodiment, the change in pixel value in the vicinity of the outline in the first localizer image that is a localizer image for calculation is milder than that in FIG. 2A and FIG. 2B. This prevents overestimation of the calculated current intensity due to the effect of the pixel value in the vicinity of the outline.

Figure 5A:
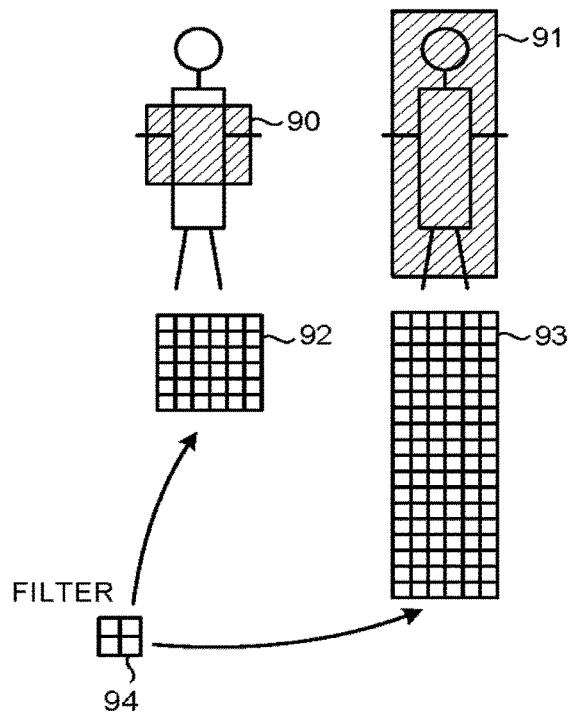

FIG. 5A illustrates a case where a scanning range 90 is the scanning range "small" and a scanning range 91 is the scanning range "large" in the same manner as in FIG. 3A. In the case of the scanning range "small", the scanning range in the channel direction (horizontal direction) is 512 mm, and the scanning range in the axial direction (vertical direction) is 512 mm, as in FIG. 3A, by way of example. In the case of the scanning range "large", the scanning range in the channel direction is 512 mm, and the scanning range in the axial direction is 1536 mm, by way of example.

In the conventional art, the matrix size is given (fixed), and the pixel dimension changes according to the scanning range. By contrast, in the embodiment, the pixel dimension is fixed, and when the scanning range changes, the matrix size changes to a variable value according to the scanning range. This will be described next.

Figure 5B:
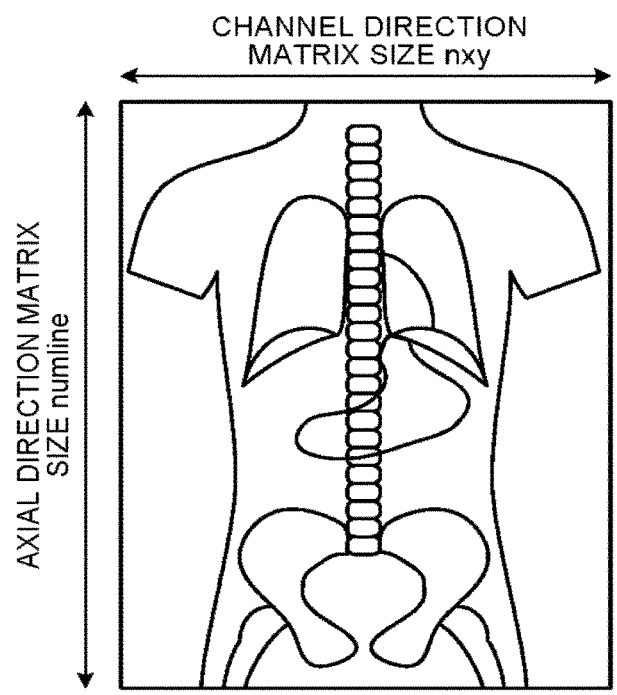

Referring to FIG. 5B, a method of determining the matrix sizes in the channel direction and the axial direction in the embodiment will be described. FIG. 5B is a diagram illustrating a method of determining the matrix sizes in the channel direction and the axial direction in the embodiment. In the case described below, the pixel dimension is 1 mm.

The localizer image generator 362 calculates the matrix size in the channel direction from the apparatus geometry. The channel direction refers to the horizontal direction illustrated, for example, in FIG. 5B. The apparatus geometry referred to here is the geometric arrangement of the X-ray tube 12a, the X-ray detector 13, and the subject P, that is, the relative positional relation therebetween. The effective imaging range in the channel direction is calculated from the apparatus geometry. For example, the place outside of the X-ray radiation range in the X-ray detector 13 is excluded from the effective imaging range. The place where the subject P is obviously absent is also excluded from the effective imaging range. The value of the effective imaging range in the channel direction can be obtained by excluding a region that is not the effective imaging range and calculating the range in which the apparatus can collect data as described above. The following relational expression holds between the effective imaging range in the channel direction, the pixel dimension in the channel direction, and the matrix size in the channel direction: "the effective imaging range in the channel direction=the pixel dimension in the channel direction×the matrix size in the channel direction". For example, when the effective imaging range in the channel direction is 1000 mm and the pixel dimension in the channel direction is 1 mm, the matrix size in the channel direction is 1000 mm/1 mm=1000. The matrix size in the channel direction is uniquely determined given the apparatus geometry and the pixel dimension in the channel direction, irrespective of the kind of organs and the like to be imaged.

The localizer image generator 362 calculates the matrix size in the axial direction from the dimension in the axial direction of the scanning range. That is, the localizer image generator 362 calculates the matrix size in the axial direction so that it is variable according to the scanning range in the axial direction. The axial direction refers to the vertical direction illustrated, for example, in FIG. 5B. The effective imaging range in the channel direction generally has a fixed value determined by the apparatus geometry, whereas the value of the imaging range in the axial direction is any value, for example, determined every time a localizer scan is performed. The following relational expression holds between the scanning range in the axial direction, the pixel dimension in the axial direction, and the matrix size in the axial direction in the sane manner in the channel direction: "the scanning range in the axial direction=the pixel dimension in the axial direction×the matrix size in the axial direction".

For example, in the case of the scanning range "small" as in a matrix 92 in FIG. 5A, that is, when the scanning range in the axial direction is 512 mm and the pixel dimension in the axial direction is 1 mm, the matrix size in the axial direction is 512 mm/1 mm=512. The matrix 92 in FIG. 5A illustrates such a situation, that is, the case where the pixel dimension is small both in the channel direction and in the axial direction.

For example, in the case of the scanning range "large" as in a matrix 93 in FIG. 5A, that is, when the scanning range in the axial direction is 1536 mm and the pixel dimension in the axial direction is 1 mm, the matrix size in the axial direction is 1536 mm/1 mm=1536. As described above, the pixel dimension is the same both in the case of the scanning range "small" and in the case of the scanning range "large". By contrast, the localizer image generator 362 calculates the matrix size in the axial direction so that it is variable according to the scanning range in the axial direction. As can be understood from these examples, since the pixel dimension is fixed, when the scanning range in the axial direction is large, the matrix size in the axial direction increases, and when the scanning range in the axial direction is small, the matrix size in the axial direction decreases.

With such a configuration, even when the scanning range is changed, the pixel dimension of the first localizer image is constant. This configuration reduces an error in calculating the value of tube current during the main scan. For example, even when the scanning range greatly exceeds 500 mm, an error in calculating the value of tube current during the main scan can be reduced. The localizer image generator 362 generates the second localizer image for display such that the pixel dimension has a constant value irrespective of the scanning range in a localizer scan.

An image processing filter 94 in FIG. 5A schematically represents a filter used in the process of calculating the tube current to be supplied to the X-ray tube 12a in the main scan. Specific examples of the image processing filter 94 include a moving average filter, a Gaussian filter, a low-pass filter, and a nonlinear filter. The localizer image generator 362 generates an image for calculating the value of tube current, using the image processing filter 94. Since the pixel dimension is constant either in the case of the scanning range "small" or in the case of the scanning range "large", the same image processing filter 94 can be used as the image processing filter 94, irrespective of the dimension of the scanning range. This configuration reduces an error in calculating the tube current.

Figure 5C:
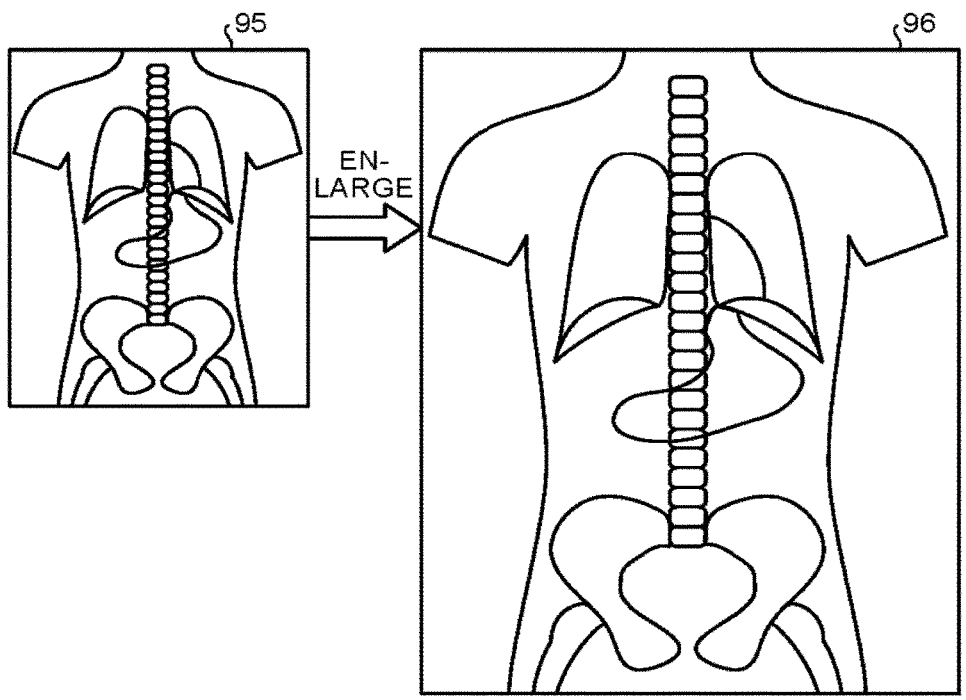

FIG. 5C is a diagram illustrating a localizer image generated by the X-ray CT apparatus according to the embodiment, in an example in which the subject P is an imaging target. An image 95 illustrated in the left diagram in FIG. 5C is an example of the first localizer image in the embodiment. An image 96 in the right diagram in FIG. 5C is a partial region of the image 95 in an enlarged view. In FIG. 5C, the image quality of the localizer image for calculation is improved as compared with that in FIG. 3B. As a result, in the present embodiment, an error in the tube current calculation can be reduced. Even when the scanning range is increased, the pixel dimension is constant and the pixel dimension is not increased, so that degradation in image quality can be prevented not only for the localizer image for calculation (the first localizer image) but also for the localizer image for display (the second localizer image). As a result, in the present embodiment, degradation in image quality of the localizer image to be displayed to the user can be prevented.

Figure 6:
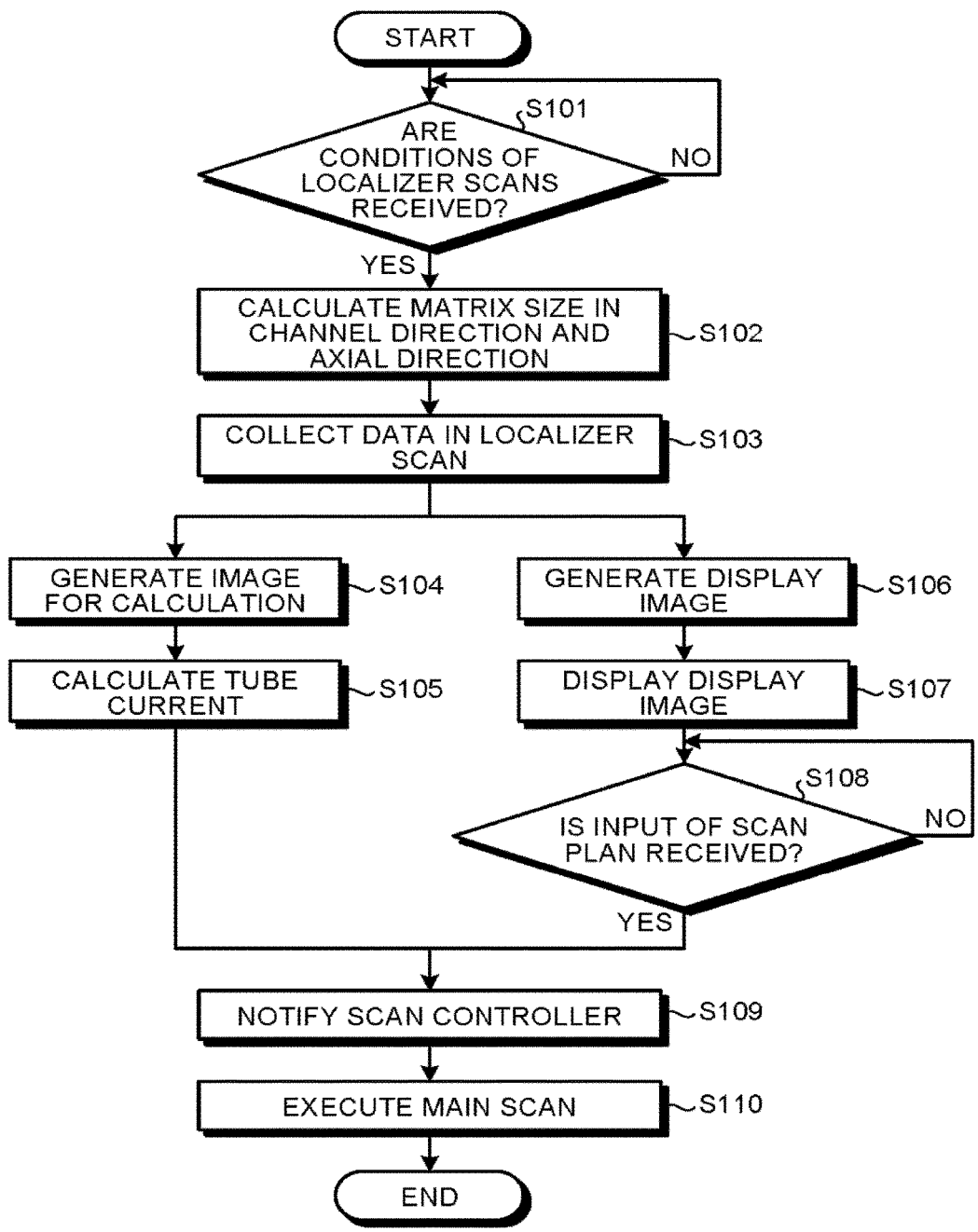
FIG. 6 and FIG. 7 are flowcharts of the procedure of processing performed by the X-ray CT apparatus according to the embodiment.
Figure 7:
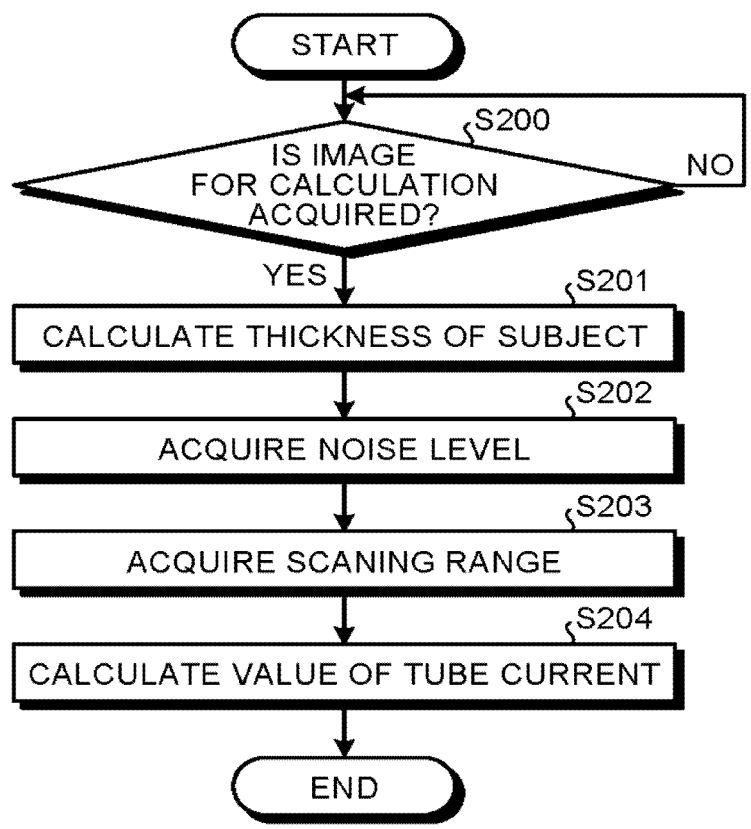

Referring now to FIG. 6 and FIG. 7, an example of the processing of the X-ray CT apparatus according to the present embodiment will be described. FIG. 6 and FIG. 7 are flowcharts of the procedure of the processing performed by the X-ray CT apparatus according to the embodiment. FIG. 6 is a flowchart of the procedure of the process performed by the controller 38 and the localizer image generator 362 in the embodiment. As illustrated in FIG. 6, the controller 38 determines whether the conditions of localizer scans are received, for example, through the input device 31 (step S101). If it is determined that the conditions of localizer scans are not received (No at step S101), the controller 38 waits until the conditions of localizer scans are received. If the conditions of localizer scans are received (Yes at step S101), the controller 38 notifies the localizer image generator 362 of the conditions of a localizer scan. The localizer image generator 362 acquires the conditions of localizer scan from the controller 38 and then calculates the matrix size in the channel direction and the matrix size in the axial direction (step S102). Specifically, as described with reference to FIG. 5B, the localizer image generator 362 calculates the matrix size in the channel direction of the localizes image from the positional relation in a localizes scan between the X-ray tube 12a, the subject P, and the X-ray detector 13. The localizes image generator 362 also calculates the matrix size in the axial (slice) direction, based on a dimension of the scanning range in the axial direction. In other word, the localizer image generator 362 serving as an acquisition unit acquires the matrix sizes in a channel direction and an axial (slice) direction of the localizes image, based on a predetermined localizer scan condition. The localizer image generator notifies the controller 38 of the calculated matrix sizes in the channel direction and in the axial direction. The controller 30 acquires the matrix size in the direction and the matrix size in the axial direction from the localizer image generator 362 and then notifies the scan controller 33 of the imaging conditions of a localizer scan. The scan controller 33 acquires the imaging conditions of a localizer scan from the controller 38 and then notifies the X-ray radiation controller 11, the gantry driver 16, the collection unit 14, the couch driver II, and other units of control information. As a result, the collection unit 14 collects data in a localizer scan (that is, a signal derived from X-rays emitted from the X-ray the 12a and transmitted through the subject P) (step S103).

The order of step S102 and step S103 may be interchanged because the matrix size in the channel direction and the matrix size in the axial direction are not parameters required at the data collecting stage but parameter for image processing after the data collection. That is, the localizer image generator 362 may calculate the matrix si in the channel direction and the matrix size in the axial direction after the controller 38 transmits the conditions of a localizer scan to the scan controller 33 to perform the localizer image data collection.

The localizer image generator 362 performs the first image processing not enhancing an outline of the imaging target, thereby generating the first localizer image (image for calculation) (step S104). For example, the localizer image generator 362 performs the first image processing using a smoothing process. In doing so, the localizer image generator 362 generates, as the first localizer image, a localizer image having a constant pixel dimension irrespective of the scanning range in the localizer image, as described with reference to FIG. 3A and FIG. 3B. This processing is performed based on the signal collected by the collection unit 14 in the localizer image and the matrix size acquired at step S102.

If the localizer image generator 36 generates a first localizer image (image for calculation), the controller 38 acquires the first localizer image (image for calculation) from the localizer image generator 362. The controller 38 calculates the value of tube current to be supplied to the X-ray tube 12*a* in the main scan, based on the first localizer image (image for calculation) (step S105). The procedure at step S105 will be detailed later.

In other words, the controller 38 calculates the value of tub current to be supplied to the X-ray tube 12*a* in the main scan, based on the first image acquired through a reconstruction process using the signal and a first filter, the signal being collected by the collection unit 14 in a localizer scan. The first filter is used in the first image processing that does not enhance the outline of the imaging target. The first filter is in contrast with the second filter used in the second image processing that enhances the outline of the imaging target.

The calculation of the value of tube current by the controller 38 means that one of the conditions for performing the processing subsequent to step S109 is satisfied.

The localizer image generator 362 performs the second image processing enhancing the outline of the imaging target, thereby generating the second localizer image (display image) (step S106). For example, the localizer image generator 362 performs the second image processing using a process including an edge detection process.

If the localizer image generator 362 has generated the second localizer image (display image), the controller 38 acquires the second localizer image (display image) from the localizer image generator 362.

In other word, the localizer image generator 362 generates the second image as a localizer image through a reconstruction process using the signal nd a second filter, the signal being collected by the collection unit 14 in a localizer scan. As previously mentioned, the second filter is a filter used in the second image processing that enhances the outline of the imaging target.

The controller 38 acquires the second localizer image (display image) from the localizer image generator 362 and then transmits data of the display image to the display 32. The display 32 receives the data of the display image and then displays the display image to the user (step S107).

The controller 38 transmits the data of the display image to the display 32 and establishes connection with the input device 31. The input device 31 receives input of a scan plan from the user. The controller 38 determines whether input of a scan plan is received from the user through the input device 31 (step S108). If it is determined that input of a scan plan is not received from the user (No at step S108), the controller 38 continuously allows the input device 31 to receive input from the user and waits until input is received. If input of a scan plan is received from the user through the input device 31 (Yes at step S108), the input device 31 notifies the controller 38 that the input of a scan plan is received and of the input scan plan. The reception, by the controller 38, of information indicating that the input of a scan plan is received from the input device 31 means that one of the conditions for performing the processing subsequent to step S109 is satisfied.

Steps S104 to S105 and step S106 to step S108 may be performed concurrently or may be performed sequentially in any given order. That is, the localizes image generator 362 may concurrently generate the first localizes image and the second localizes image. The localizer image generator 362 may sequentially generate the first localizes image and the second localizes image in any given order. In the concurrent processing, these processes are not necessarily performed simultaneously.

If the two processes described above, that is, the tube current calculation (step S105) and the reception of the input of a scan plan (Yes at step S108) are finished, the controller 38 notifies the scan controller 33 of the calculated value of tube current and the input scan plan (step S109). The scan controller 33 controls the X-ray radiation controller 11, the gantry driver 16, the collection unit 14, the couch driver 21, and other units in accordance with the value of tube current and the scan plan received from the controller 38. In this manner, the main scan is executed (step S110). The process then ends. In the present embodiment, imaging in a plurality of directions is received at step S101 as a condition of a localizes scan. The processing at step S102, step S103, step S104, step S106, and step S107 is performed in each of the received directions, and the processing at step S105 is performed using the first localizer image in each of the directions.

The processing performed by the controller 38 of the X-ray CT apparatus according to the embodiment using the localizer image generated by the localizer image generator 362 will now be described. The controller 38 acquires the first localizer image as an image for calculation from the localizer image generator 362, then calculated the thickness of the subject P using the fret localizer image, and calculates the value of tube current based on the calculated thickness. FIG. 7 is a flowchart of the procedure of this process. The flowchart in FIG. 7 details the process performed by the controller 36 at step S105 in FIG. 6.

As illustrated in FIG. 7, the controller 38 determines whether an image for calculation is acquired from the localizer image generator 362 (step S200). If the localizer image generator 36 has not yet generated an image for calculation, the controller 38 does no acquire an image for calculation (No at step S200) and waits until the localizer image generator 362 generates an image for calculation. If the localizer image generator 362 generates an image for calculation, the controller 38 acquires the image for calculation (Yes at step S200) and calculates the thickness of the subject P (step S201). The controller 38 calculates the thickness of the subject P for each view. For example, the controller 38 calculates the thickness of the subject P, assuming that the cross section of the subject is oval.

Upon calculating the thickness of the subject P based on the image for calculation at step S201, the controller 38 acquires a set value of noise level of an image during the main scan, for example, from the input device 31, the image storage 37, or a database not illustrated (step S202). The controller 38 then acquires the scanning range in the main scan (step S203). For example, the controller 38 receives input of the imaging position and the scanning rang in the main scan from the user through the input device 31. Prior to this, the controller 38 displays the display image generated at step S106 to the user, if necessary, through the display 32.

Step S201 to step S203 are not necessarily performed in this order. For example, the controller 38 may acquire the noise level at step S202 after calculating the thickness of the subject at step S201 and acquiring the scanning ran at step S203. Step S201 to step S203 are not necessarily processed sequentially in this order but may be processed concurrently.

If the thickness of the subject P is calculated and the noise level and the scanning range are acquired, the controller 38 calculates the value of tube current based on the thickness of the subject P and the set noise level (step S204). Specifically, the controller 38 calculates the value of tube current in order that the noise level of the image in the main scan, expected to be generated when the main scan is performed, attains a predetermined level. That is, given that if the thickness of the subject P and the value of tube current are determined, the noise level expected when imaging is performed under the conditions is uniquely determined, the controller 38 calculates the value of tube current expected to achieve the given noise level, using the thickness of the subject P and the noise level as given parameters. If the value of tube current is calculated, the process performed by the controller 38 is finished. In the present embodiment, the first localizer image in each of a plurality of directions is acquired at step S200, and the processing subsequent to step S201 is performed using the first localizer image for each of those directions.

As described above, in the present embodiment, the controller 38 calculates the value of tube current by AEC, using a localizer image as an image for calculation in which the signal value of the outline portion is not enhanced and the pixel dimension is constant irrespective of the scanning range in localizer scan. The present embodiment thus can reduce an error in calculating the value of tube current to be supplied to the X-ray tube 12a.

Other Embodiments

In the foregoing embodiment, the localizer image generator 362 performs the first image processing that does not enhance the outline of the imaging target to generate the first localizer image (image for calculation). When the localizer image generator 362 generates an image for calculation, the controller 38 acquires the image for calculation from the localizer image generator 362 and calculates the value of tube current to be supplied to the X-ray tube 12a in the main scan, based on the image for calculation. However, embodiments are not limited thereto. For example, the controller 38 may calculate the value of tube current based on raw data (that is, the signal collected by the collection unit. 14 in a localizer scan).

Figure 8:
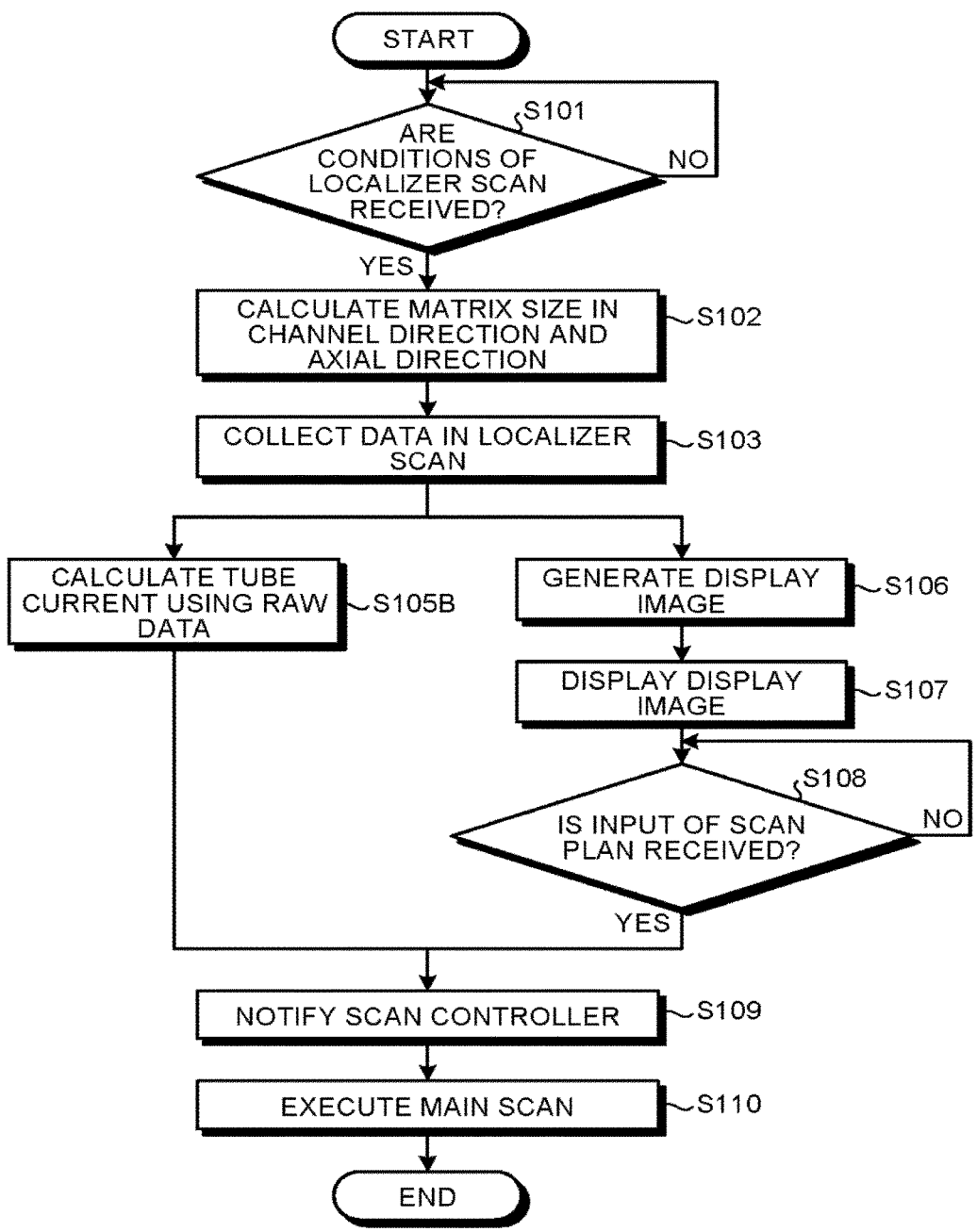
FIG. 8 is a flowchart of the procedure of processing performed by the X-ray CT apparatus according to another embodiment.

FIG. 8 is a flowchart of the processing performed by the X-ray CT apparatus according to another embodiment.

The detailed description of the same processing as the processing described in FIG. 6 is omitted as appropriate.

As described with reference to FIG. 6, the controller 38 determines whether the conditions of a localizer scan are received, for example, through the input device 31 (step S101). The localizer image generator 362 then calculates the matrix size in the channel direction of the localizer image, based on the positional relation in the localizer scan between the X-ray tube 12a, the subject. P, and the X-ray detector 13, in the same manner as in FIG. 6. The localizer image generator 362 calculates the matrix size in the axial (slice) direction, based on a dimension of the scanning range in the axial direction (step S102). In other words, the localizes image generator 362 serving as an acquisition unit acquires the matrix sizes in the channel direction and the axial (slice) direction of the localizes image, based on a predetermined localizes scan condition. The collection unit 14 then collects a signal derived from X-rays emitted from the X-ray tube 12a and transmitted through the subject (step S103).

Similarly, the localizes image generator 362 generates a localizes image (display image) through a reconstruction process using the signal and a filter (corresponding to "the second filter" in FIG. 6), the signal being collected by the collection unit 14 in a localizes scan (step S106). The controller 38 acquires the display image from the localizes image generator 362 and then transmits data of the display image to the display 32. The display 32 receives the data of the display image and then displays the display image to the user (step S107). The controller 38 transmits the data of the display image to the display 32 and establishes connection with the input device 31. The controller 38 determines whether input of a scan plan is received from the user through the input device 31 (step S108). If the input of a scan plan is received from the user (Yes at step S108), the input device 31 notifies the controller 38 that the input of a scan plan is received and of the input scan plan. This configuration satisfies one of the conditions for performing the processing subsequent to step S109.

Unlike the process described with reference to FIG. 6, in the X-ray CT apparatus according to the embodiment, if the collection unit 14 collects data (signal) in a localizer scan at step S103, the controller 38 directly calculates the value of tube current to be supplied to the X-ray tube in the main scan, without undergoing image generation, based on the data (signal) collected by the collection unit 14 in a localizes scan. That is, the controller 38 directly calculates the tube current using raw data (step S105B).

As an example, the controller 38 acquires data values of raw data and a table of optimum values of tube current corresponding to the data values, from the image storage 37 in which the table is stored in advance. When the pre-processing unit 34 performs processing on the data collected by the collection unit 14 and generates corrected projection data (raw data), the controller 38 calculates an optimum value of tube current based on the raw data and the table.

If the tube current calculation using the raw data (step S105B) and the reception of the input of a scan plan (Yes at step S108) are finished, the controller 38 notifies the scan controller 3 of the calculated value of tube current and the input scan plan (step S109). The scan controller 33 controls the X-ray radiation controller 11, the gantry driver 16, the collection unit 14, the couch driver 21, and other units. In this manner, the main scan is executed (step S110). The process then ends.

Although the controller 38 directly calculates the tube current using the raw data at step S105B in the foregoing description, embodiments are no limited thereto. For example, the controller may calculate the tube current using pure raw data that is data before processing is performed by the pre-processing unit 34. As an example, the controller 38 may calculate the tube current using a count obtained by subtracting the count of imaging performed with the subject P lying on the couchtop 22 from the count of all air (the state in which the subject P does not lie on the couchtop 22).

In the example described in the embodiment, the localizes image generator 362 calculates the tube current without image generation. This configuration reduces the calculation load involved in image generation. Inclusion of noise in the image generation process can be prevented.

Although a localizer scan is performed in a plurality of directions in the examples described in the foregoing embodiments, embodiments are not limited thereto. For example, a localizer scan may be performed in one direction, and the controller 38 may calculate the value of tube current using the localizer image in one direction generated by the localizer image generator 362. The components in the illustrated apparatuses are conceptual functions and are not necessarily physically configured as illustrated in the figures. That is, the specific manner of distribution and integration of the apparatuses is not limited to those illustrated in the figures but all or some of the apparatuses may be functionally or physically distributed or integrated in any units depending on various loads and use conditions. All or some of the processing functions performed in each apparatus may be implemented by a CPU and a program analyzed and executed in the CPU or may be implemented as hardware with wired logic.

The image processing performed by the X-ray CT apparatus according to the embodiments may be implemented by executing a program prepared in advance with a computer such as a personal computer and a workstation. The program may be distributed through a network such as the Internet. The program may be recorded on a computer-readable non-transitory recording medium such as a hard disk, a flexible disk (FD), a CD-ROM, an MO, and a DVD and read from the recording medium by a computer for execution.

The embodiments described above can reduce an error in calculating the value of tube current to be supplied to the X-ray tube.

While certain embodiments have been described, these embodiments have been presented by way of example only, and are not intended to limit, the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography (CT) apparatus comprising:
    collection circuitry configured to collect a signal derived from X-rays emitted from an X-ray tube and transmitted through a subject;
    control circuitry configured to calculate a value of tube current to be supplied to the X-ray tube in a main scan, based on a first image acquired through a first reconstruction process, the first reconstruction process using the signal and a first image-processing filter, the signal being collected by the collection circuitry in a localizer scan; and
    image generation circuitry configured to generate a second image as a localizer image through a second reconstruction process, the second reconstruction process using the signal and a second image-processing filter, the signal being collected by the collection circuitry in the localizer scan.

2. The X-ray CT apparatus according to claim 1, further comprising acquisition circuitry configured to acquire matrix sizes in a channel direction and a slice direction of the localizer image, based on a predetermined localizer scan condition, wherein
    the image generation circuitry is configured to generate, as the first image, a localizer image having a constant pixel dimension irrespective of a scanning range in the localizer scan, based on the signal collected by the collection circuitry in the localizer scan and the matrix sizes.

3. The X-ray CT apparatus according to claim 2, wherein the image generation circuitry
    is configured to calculate the matrix size in the channel direction of the localizer image from a positional relation in the localizer scan between the X-ray tube, the subject, and an X-ray detector that detects X-rays transmitted through the subject and
    is configured to calculates the matrix size in the slice direction of the localizer scan, based on a dimension of the scanning range in the slice direction.

4. The X-ray CT apparatus according to claim 1, wherein the image generation circuitry is configured to perform first image processing not enhancing an outline of an imaging target, thereby generating the first image, and is configured to perform second image processing enhancing the outline of the imaging target, thereby generating the second image.

5. The X-ray CT apparatus according to claim 4, wherein the image generation circuitry is configured to perform the first image processing using a smoothing process and is configured to perform the second image processing using a process including an edge detection process.

6. The X-ray CT apparatus according to claim 1, wherein the image generation circuitry is configured to concurrently generate the first image and the second image.

7. The X-ray CT apparatus according to claim 1, wherein the image generation circuitry is configured to sequentially generate the first image and the second image in any given order.

8. An X-ray computed tomography (CT) apparatus comprising;
    collection circuitry configured to collect a signal derived from X-rays emitted from an X-ray tube and transmitted through a subject;
    image generation circuitry configured to generate a localizer image through a reconstruction process, the reconstruction process using the signal and an image-processing filter, the signal being collected by the collection circuitry in a localizer scan;
    control circuitry configured to calculate a value of tube current to be supplied to the X-ray tube in a main scan, based on the signal collected by the collection circuitry in the localizer scan; and
    acquisition circuitry configured to acquire matrix sizes in a channel direction and a slice direction of the localizer image, based on a predetermined localizer scan condition, wherein
    the image generation circuitry is configured to generate the localizer image having a constant pixel dimension irrespective of a scanning range in the localizer scan, based on the signal collected by the collection circuitry in the localizer scan and the matrix sizes.

9. The X-ray CT apparatus according to claim 8, wherein the image generation circuitry
    is configured to calculate the matrix size in the channel direction of the localizer image, based on a positional relation in the localizer scan between the X-ray tube, the subject, and an X-ray detector that detects X-rays transmitted through the subject and
    is configured to calculate the matrix size in the slice direction of the localizer image based on a dimension of the scanning range in the slice direction.

* * * * *